United States Patent [19]

Saito et al.

[11] Patent Number: 4,923,501
[45] Date of Patent: May 8, 1990

[54] PYRIMIDINE DERIVATIVES, PROCESSES FOR THEIR PRODUCTION, AND HERBICIDAL METHOD AND COMPOSITIONS

[75] Inventors: Yoshihiro Saito; Nobuhide Wada, both of Kakegawa; Shoji Kusano, Hamamatsu; Takeshige Miyazawa; Satoru Takahashi, both of Shizuoka; Yasuhumi Toyokawa, Tokyo; Ikuo Kajiwaca, Nagaokakyo, all of Japan

[73] Assignees: Kumiai Chemical Industry Co., Ltd.; Ihara Chemical Industry Company, Ltd., both of Tokyo, Japan

[21] Appl. No.: 264,015

[22] Filed: Oct. 28, 1988

[30] Foreign Application Priority Data

Nov. 4, 1987 [JP] Japan ................... 62-278894

[51] Int. Cl.$^5$ .................. A01N 43/54; C07D 239/60
[52] U.S. Cl. ........................ 71/92; 544/225; 544/299; 544/301; 544/302; 544/303
[58] Field of Search ............ 544/225, 299, 301, 302, 544/303; 71/92

[56] References Cited

U.S. PATENT DOCUMENTS 4,427,437  1/1984  Serban ........................ 544/299
4,770,691  9/1988  Nezu et al. ..................... 71/92

OTHER PUBLICATIONS

Solomons et al., Org. Chem. 3rd Edition, pp. 853 and 855.
Serban et al., CA92-175773f (1980).
"Certain Pyrimidine Derivatives for Inhibiting the Growth of Plants", Nezu et al., CA107-134322t (1987).
"Preparation of Pyrimidinyloxybenzoates and -Thiobenzoates as Herbicides".

Primary Examiner—Cecilia Shen
Attorney, Agent, or Firm—Oblon, Spivak, McClelland, Maier & Neustadt

[57] ABSTRACT

A pyrimidine derivative having the formula:

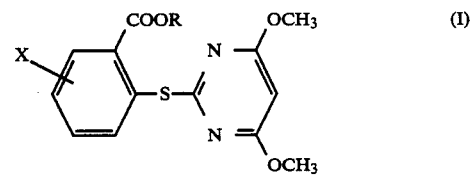

wherein X is a halogen atom, a lower alkyl group or a phenoxy group (wherein said phenoxy group may be substituted by halogen, lower alkyl or lower alkoxy), and R is a hydrogen atom, a lower alkyl group, an alkoxyalkyl group, a benzyloxyalkyl group, an alkoxycarbonyl alkyl group, a cyanoalkyl group or a

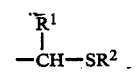

group (wherein $R^1$ is a hydrogen atom or a lower alkyl group, and $R^2$ is a lower alkyl group or a phenyl group which may be substituted by nitro), or a salt thereof.

12 Claims, No Drawings

PYRIMIDINE DERIVATIVES, PROCESSES FOR THEIR PRODUCTION, AND HERBICIDAL METHOD AND COMPOSITIONS

The present invention relates to novel pyrimidine derivatives or their salts, processes for their production, herbicidal compositions containing them, and a herbicidal method for applying them.

Recently, a number of herbicides have been developed and practically used, and they have contributed to the saving of energy for the agricultural operations and to the improvement of the production efficiency. Further, it has been known that various 2-phenoxypyrimidine derivatives are effective as herbicides ((1) Japanese Unexamined Patent Publication No. 174059/1987, (2) Japanese Unexamined Patent Publication No. 55729/1979 and (3) Agr. Biol. Chem., Vol. 30, No. 9, p. 896 (1966)).

However, the compounds disclosed in the above reference (1) have a problem with respect to the safety to crop plants, although they exhibit high herbicidal effects. On the other hand, the compounds disclosed in the above references (2) and (3) have drawbacks that their herbicidal activities against annual weeds are inadequate, and they exhibit no substantial activities against perennial weeds.

The present inventors have conducted extensive research on pyrimidine derivatives with an aim to develop a compound having more excellent herbicidal activities, and as a result, have found that the compounds of the present invention having substituents introduced at specific positions of the pyrimidine and benzene rings of phenylthiopyrimidine derivatives, exhibit excellent herbicidal effects against perennial weeds as well as annual weeds, and at the same time, they have a high level of safety to crop plants, particularly to cotton. The present invention has been accomplished on the basis of these discoveries.

The present invention provides a pyrimidine derivative having the formula:

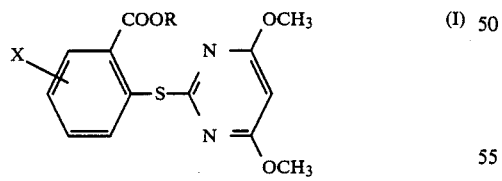
(I)

wherein X is a halogen atom such as chlorine, bromine, iodine or fluorine, a lower alkyl group, preferably a $C_1$-$C_4$ alkyl group, or a phenoxy group (wherein said phenoxy group may be substituted by halogen such as chlorine, bromine, iodine or fluorine, lower alkyl, preferably $C_1$-$C_4$ alkyl, or lower alkoxy, preferably $C_1$-$C_4$ alkoxy), and R is a hydrogen atom, a lower alkyl group, preferably a $C_1$-$C_6$ alkyl group, an alkoxyalkyl group, preferably a $C_1$-$C_4$ alkoxy $C_1$-$C_4$ alkyl group, a benzyloxyalkyl group, preferably a benzyloxy $C_1$-$C_4$ alkyl group, an alkoxycarbonylalkyl group, preferably a $C_1$-$C_4$ alkoxy carbonyl $C_1$-$C_4$ alkyl group, a cyanoalkyl group or a

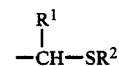

group (wherein $R^1$ is a hydrogen atom or a lower alkyl group, preferably a $C_1$-$C_4$ alkyl group and $R^2$ is a lower alkyl group, preferably a $C_1$-$C_4$ alkyl group or a phenyl group which may be substituted by nitro), or a salt thereof.

The present invention also provides a herbicidal composition comprising a herbicidally effective amount of a pyrimidine derivative of the formula I or a salt thereof, and an agricultural adjuvant.

Further, the present invention provides a method for killing weeds which comprises applying a herbicidally effective amount of a pyrimidine derivative of the formula I or a salt thereof to a locus to be protected.

Now, the present invention will be described in detail with reference to the preferred embodiments In the formula I, X is preferably substituted at the 6-position. Particularly preferred as X is a chlorine atom, a methyl group or a fluorine atom at the 6-position. R is preferably a hydrogen atom, a lower alkyl group, an alkoxyalkyl group or a benzyloxyalkyl group. Particularly preferred as R is a hydrogen atom. Among the compounds of the formula I, those represented by the following formulas I-1 and I-2 are preferred:

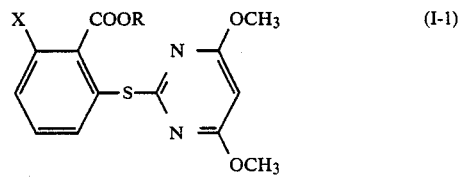
(I-1)

wherein R is as defined in claim 1, and X is a halogen atom or a lower alkyl group.

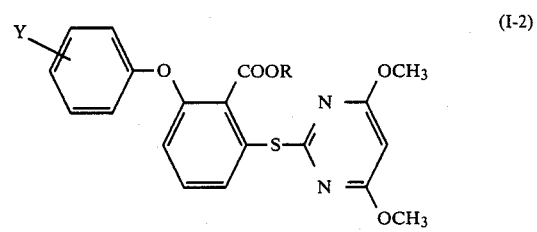
(I-2)

wherein R is as defined in claim 1, and Y is a hydrogen atom, a halogen atom, a lower alkyl group or a lower alkoxy group.

Now, typical examples of the compound of the present invention will be presented in Table 1. Compound Nos. given in the Table will be referred to in the subsequent description in the specification.

TABLE 1
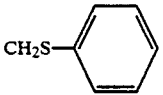
| No | R | X | Melting point (°C.) or Refractive index |
|----|---|---|---|
| 1 | H | 6-Cl | 148–151 |
| 2 | H | 6-CH$_3$ | 131–132 |
| 3 | CH$_3$ | 6-Cl | $n_D^{20}$ = 1.5770 |
| 4 | CH$_3$ | 6-CH$_3$ | $n_D^{20}$ = 1.5775 |
| 5 | H | 5-CH$_3$ | 177–182 |
| 6 | 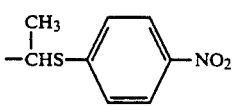 | 6-Cl | $n_D^{20}$ = 1.6166 |
| 7 | CH$_3$ | 5-CH$_3$ | 71–72 |
| 8 | H | 5-Cl | 203–206 |
| 9 | H | 3-Cl | 128–131 |
| 10 | H | 6-F | 133–135 |
| 11 | CH$_3$ | 6-F | 45–47 |
| 12 | CH$_2$OCH$_3$ | 6-Cl | 70–72 |
| 13 | CH$_2$SCH$_3$ | 6-Cl | 94–95 |
| 14 | H | 3-CH$_3$ | 144–153 |
| 15 | 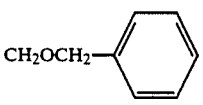 | 6-Cl | $n_D^{20}$ = 1.6273 |
| 16 | C$_2$H$_5$ | 6-Cl | 70–75 |
| 17 | CH$_2$OC$_2$H$_5$ | 6-Cl | $n_D^{20}$ = 1.5590 |
| 18 | 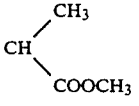 | 6-Cl | $n_D^{20}$ = 1.5826 |
| 19 | 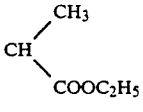 | 6-Cl | Not measurable |
| 20 | 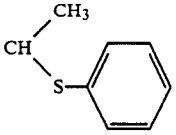 | 6-Cl | $n_D^{20}$ = 1.5483 |
| 21 | 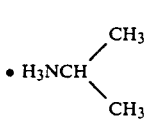 | 6-Cl | $n_D^{20}$ = 1.6041 |
| 22 | CH$_2$CN | 6-Cl | 97–105 |
| 23 | C$_4$H$_9$-i | 6-Cl | 68–70 |
| 24 | •H$_3$NCH(CH$_3$)$_2$ | 6-Cl | 149–151 |
| 25 | •HN(C$_2$H$_4$OH)$_3$ | 6-Cl | 94–101 |
| 26 | •Na | 6-Cl | 246-14 250 |
| 27 | •H$_2$N(C$_2$H$_4$OH)$_2$ | 6-Cl | Not measurable |

TABLE 1-continued

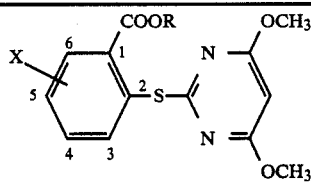

| No | R | X | Melting point (°C.) or Refractive index |
|---|---|---|---|
| 28 | (structure with Cl, COO⁻, OCH₃, S, N, OCH₃)₃ Fe³⁺ | | 140–145 |
| 29 | (structure with Cl, COO⁻, OCH₃, S, N, OCH₃)₂ Ca²⁺ | | 172–175 |
| 30 | H | 6-O-phenyl | |
| 31 | H | 6-O-(2-methylphenyl) | 124–127 |
| 32 | • NH₄ | 6-Cl | 150–154 |
| 33 | H | 6-O-(3-chlorophenyl) | |
| 34 | H | 6-O-(4-methoxyphenyl) | |

Among the compounds of the present invention, benzoic acid derivatives wherein R is a hydrogen atom, or their salts exhibit particularly excellent herbicidal effects.

The salts may be alkali metal salts, alkaline earth metal salts, transition metal salts or organic ammonium salts.

Compound Nos. 1, 2, 11, 12, 17, 18, 21 and their salts are particularly superior in that they have excellent herbicidal activities and no substantial phytotoxicity against crop plants, particularly cotton.

The compound of the present invention can be prepared in accordance with the following process.

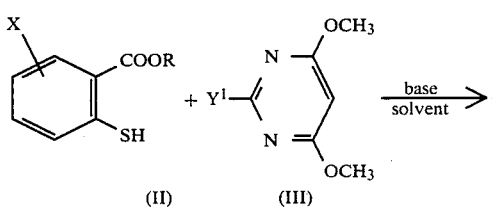

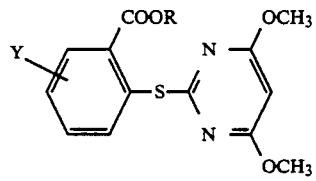

(I)

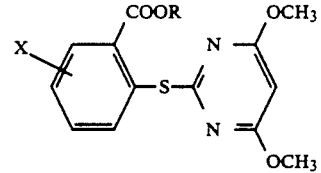

(I)

In the formulas, $Y^1$ is a halogen atom, an alkylsulfonyl group or a substituted or unsubstituted benzylsulfonyl group, and X and R are as defined above.

The compound of the formula I of the present invention can be prepared by reacting the compound of the formula II with the compound of the formula III in the presence of a base, preferably in a solvent, at a temperature within a range of from room temperature to the boiling point of the solvent for 1 to 24 hours. When the reaction is conducted without a solvent, the reaction can be conducted by using an alkali metal carbonate as a base, such as anhydrous potassium carbonate at a temperature within a range of from 120° to 160° C.

The solvent used for this reaction includes, for example, a hydrocarbon solvent such as benzene, toluene or xylene, a halogenated hydrocarbon such as methylene chloride or chloroform, an alcohol solvent such as methanol, ethanol, isopropanol, an ether solvent such as ethyl ether, isopropyl ether, tetrahydrofuran or 1,4-dioxane, a ketone solvent such as acetone or methyl ethyl ketone, an ester solvent such as methyl acetate or ethyl acetate, an aprotic non-polar solvent such as N,N-dimethylformamide, N,N-dimethylacetamide or dimethylsulfoxide and acetonitrile, and water.

As the base, there may be mentioned an alkali metal such as sodium metal or potassium metal, an alkali metal hydride or an alkaline earth metal hydride such as sodium hydride, potassium hydride or calcium hydride, a carbonate such as sodium carbonate, potassium carbonate, sodium hydrogencarbonate or potassium hydrogencarbonate and a metal hydroxide such as sodium hydroxide or potassium hydroxide.

Further, the compound of the present invention can also be prepared in accordance with the following process.

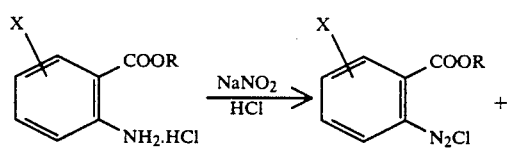

(IV)  (V)

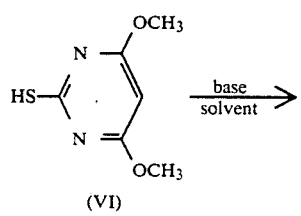

(VI)

In the above formulas, R and X are as defined above.

The compound of the formula I can be prepared by reacting the diazonium salt of the formula V converted from the compound of the formula IV, with the compound of the formula VI in a basic solution at a low temperature, preferably within a temperature range of from $-20°$ to $10°$ C.

As the diazonium salt, a hydroborate, a hydroiodate, a tetrafluoroborate or a sulfate can be used in addition to the hydrochloride. Further, the basic solution can be prepared by an addition of a strong base such as sodium hydroxide, potassium hydroxide, barium hydroxide or calcium hydroxide to a solvent.

The 2-[(4,6-dimethoxypyrimidin-2-yl)thio]benzoic acid derivative of the formula I prepared by the above processes, may be reacted with sodium hydrogen carbonate sodium hydroxide, potassium hydroxide, sodium hydride or the like to convert it to its alkali metal salt. Then, calcium chloride may be reacted to the alkali metal salt, or calcium carbonate or calcium hydride may be reacted to the corresponding benzoic acid to obtain an alkaline earth metal salt. Further, iron chloride or the like is reacted to the alkali metal salt to convert it to a transition metal salt such as an iron salt.

Further, it is possible to convert the benzoic acid to an organic ammonium salt by reacting it with an aliphatic amine such as a primary amine, a secondary amine, a tertiary amine, diethanol amine, triethanol amine, an alkoxyalkylamine, a cyclohexylamine or morphorine, or with an aromatic amine such as aniline or naphthylamine.

Now, the present invention will be described in further detail with reference to Examples. However, it should be understood that the present invention is by no means restricted to specific Examples.

EXAMPLE 1

Preparation of 2-[(4,6-dimethoxypyrimidin-2-yl)thio]6-methylbenzoic acid (Compound No. 2)

5.0 g of 2-amino-6-methylbenzoic acid hydrochloride was converted to a diazonium salt with concentrated hydrochloric acid and 2.3 g of sodium nitrite. Then, this diazonium salt was gradually dropwise added to a previously prepared sodium disulfide solution (which was prepared from 8.7 g of sodium sulfide nonahydrate, 1.1 g of sulfur, 1.5 g of sodium hydroxide and 15 ml of water) at from 0° to 5° C. After the completion of the dropwise addition, the mixture was stirred at room temperature for 2 hours to complete the reaction. The reaction solution was poured into a large amount of water, and concentrated hydrochloric acid was added thereto. Then, the mixture was extracted with ethyl acetate. A sodium hydrogen carbonate aqueous solution was added to the ethyl acetate layer, and sodium hydrogencarbonate-soluble components were extracted. 5.8 g of sodium pyrosulfate was added to the aqueous solution, and the mixture was refluxed for 30 minutes to complete the reaction. Concentrated hydrochloric acid was added to the reaction solution, and then the mixture was extracted with ethyl acetate. The extract was dried, and then the solvent was distilled off under reduced pressure to obtain 3.6 g (yield: 65%) of 2-mercapto-6-methylbenzoic acid.

Then, 3.6 g of 2-mercapto-6-methylbenzoic acid, 4.7 g of 4,6-dimethoxy-2-methylsulfonylpyrimidine and 3.5 g of unhydrous potassium carbonate were dissolved in 20 ml of dimethylformamide, and then the mixture was stirred at from 110 to 120° C. for one hour. The reaction solution was poured into a large amount of water, and concentrated hydrochloric acid was added thereto. Then, the mixture was extracted with chloroform. The chloroform layer was washed with water and dried, and then the solvent was distilled off under reduced pressure. The crude crystals were purified by column chromatography by using a developing solvent of hexane/ethyl acetate and recrystallized from ethyl acetate to obtain 0.8 g of 2-[(4,6-dimethoxypyrimidin-2-yl)thio]-6-methylbenzoic acid as white powder. Melting point: 131°–132° C.

EXAMPLE 2

Preparation of 2-chloro-6-[(4,6-dimethoxypyrimidin-2-yl)thio]benzoic acid (Compound No. 1)

5.0 g of 2-amino-6-chlorobenzoic acid hydrochloride was converted to a diazonium salt with 2.3 g of sodium nitrite and concentrated hydrochloric acid. Then, this diazonium salt was gradually dropwise added to a solution comprising 4.8 g of 4,6-dimethoxy-2-mercaptopyrimidine, 2.4 g of sodium hydroxide and 40 ml of water at 0° C. After completion of the dropwise addition, the mixture was stirred at room temperature for 2 hours to complete the reaction. Concentrated hydrochloric acid was added to the reaction solution, and then, the mixture was extracted with ethyl acetate. The extract was dried, and then the solvent was distilled off under reduced pressure. The residue thereby obtained was purified by column chromatography to obtain 1.8 g of 2-chloro-6-[(4,6-dimethoxypyrimidin-2-yl)thio]benzoic acid as ocher powder. Melting point: 148°–151° C.

EXAMPLE 3

Preparation of triethanolammonium 2-chloro-6-[(4,6-dimethoxypyrimidin-2-yl)thio]benzoate (Compound No. 25)

1.57 g of 2-chloro-6-[(4,6-dimethoxypyrimidin-2-yl)thio]benzoic acid and 0.72 g of triethanolamine were dissolved in 20 ml of tetrahydrofuran, and the solution was stirred at room temperature for 30 minutes. The solvent was distilled off from this solution, and isopropyl ether was added to the residue to solidify it. The solid was separated by filtration and then dried to obtain 2.0 g of triethanolammonium 2-chloro-6-[(4,6-dimethoxypyrmidin-2-yl)thio]benzoate as white solid. Melting point: 94°–101° C.

The herbicidal composition of the present invention comprises a herbicidally effective amount of the compound of the present invention and an agricultural adjuvant. The herbicide of the present invention may be used as it is or may be formulated in various formulations such as a wettable powder, a granule, an emulcifiable concentrate or a dust by blending it with a carrier, a surfactant, a dispersing agent or an adjuvant which is commonly employed for the formulation of agricultural chemicals.

As the carrier to be used for the formulation, there may be mentioned a solid carrier such as jeeklite, talc, bentonite, clay, kaolin, diatomaceous earth, white carbon, vermiculite, slaked lime, silica sand, ammonium sulfate or urea, or a liquid carrier such as isopropyl alcohol, xylene, cyclohexane or methyl naphthalene. As the surfactant and dispersing agent, there may be mentioned, for example, an alcohol-sulfuric acid ester, an alkyl aryl sulfonate, lignin sulfonate, a polyoxyethylene glycol ether, a polyoxyethylene alkyl aryl ether or a polyoxyethylene sorbitol mono-alkylate. As the adjuvant, for example, carboxymethyl cellulose, polyethylene glycol or gum arabic may be mentioned. In practical use, such a herbicide may be diluted to a suitable concentration before application, or may directly be applied.

The herbicide of the present invention may be used in combination with other herbicides.

The herbicide of the present invention is applied to weeds in a paddy field by irrigated soil treatment before or after the emergence of weeds or by foliage treatment. Further, the herbicide is applied to weeds in an upland field or a non-agricultural field by soil treatment before or after the emergence of weeds or by foliage treatment.

For soil treatment, the herbicide of the present invention is applied in a dose of from 1 g to 1 kg of the active ingredient per 10 ares. For foliage treatment, it is diluted to a concentration of from 1 to 10,000 ppm and applied in a dose of from 1 g to 1 kg of the active ingredient per 10 ares.

Now, Formulation Examples for the herbicidal composition of the present invention will be given. However, it should be understood that the present invention is by no means restricted to these specific Examples. In these Examples, "%" means "% by weight".

FORMULATION EXAMPLE 1 (wettable powder)

10% of Compound No. 1, 0.5% of Emulgen 810 (trademark, Kao Corporation), 0.5% of Demol N (trademark, Kao Corporation), 20% of Kunilite 201 (trademark, Kunimine Kogyo K.K.) and 69% of Jeeklite CA (tradename, Jeeklite Company Ltd.) were uniformly mixed and pulverized to obtain a wettable powder.

FORMULATION EXAMPLE 2 (emulsifiable concentrate)

30% of Compound No. 1, 20% of cyclohexanone, 11% of polyoxyethylene alkyl aryl ether, 4% of calcium alkylbenzenesulfonate and 35% of methyl naphthalene, were uniformly dissolved to obtain an emulsifiable concentrate.

FORMULATION EXAMPLE 3 (granule)

5% of Compound No. 1, 2% of a sodium salt of a lauryl alcohol-sulfuric acid ester, 5% of sodium lignin sulfonate, 2% of carboxymethyl cellulose and 86% of clay were uniformly mixed and pulverized. To 100 parts by weight of this mixture, 20 parts by weight of water was added, and the mixture was kneaded, and granulated into granules of from 14 to 32 mesh by means of an extrusion granulating machine, followed by drying to obtain granules.

FORMULATION EXAMPLE 4 (dust)

2% of Compound No. 2, 5% of diatomaceous earth and 93% of clay were uniformly mixed and pulverized to obtain a dust.

The compounds and the herbicidal compositions of the present invention are capable of effectively controlling annual weeds such as barnyardgrass (*Echinochloa crus-qalli*), flatsedge (*Cyperus difformis*), monochoria (*Monochoria vaginalis*), and perennial weeds such as bulrush (*Scirpus hotarui*) *Alisma canaliculatum*, *Cyperus serotinus*, *Sagittaria pvqmaea* and *Eleocharis kuroguwai*, grown in paddy fields. Further, they are capable of effectively controlling annual weeds such as barnyardgrass (*Echinochloa crus-galli*), crabgrass (*Digitaria sanquinalis*), goosegrass (*Eleusine indica*), green foxtail (*Setaria viridis*), water foxtail (*Alopecurus aequalis*), annual bluegrass (*Poa annua*), wild oat (*Avena fatua*), italian ryegrass (*Lolium multiflorum*), smartweed (*Polygonum lapathifolium*), slender amaranth (*Amaranthus viridis*), lambsquarters (*Chenooodium album*), velvetleaf (*Abutilon theophrasti*), prickly sida (*Sida spinosa*), sicklepod (*Cassia tora*), chickweed (*Stellaria media*), morningglory (*Ipomoea spp*), common cocklebur (*Xanthium strumarium*), rice flatsedge (*Cyperus iria*), broadleaf signalgrass (*Brachiaria platyphylla*), itchgrass (*Rottoboellia exaltata*), downy brome (*Bromus tectorum*), wild buckwheat (*Polygonum convolvulus*), wild mustard (*Brassica arvensis*) and devils beggarticks (*Bidens frondosa*), and perennial weeds such as purple nutsedge (*Cyperus rotundus*), johnsongrass (*Sorghum haleoense*), bermudagrass (*Cynodon dactylon*) and quackgrass (*Agropyron repens*) grown in upland fields. On the other hand, the safety to crop plants, particularly to cotton are high.

When the herbicide of the present invention is used as a herbicide for cotton, it has the following features. Further, when it is used as a herbicide for crop plants other than cotton, it also has various merits.

(1) The herbicide of the present invention is highly safe to cotton in each treatment of soil treatment before the emergence of weeds and foliage treatment after the emergence of weeds. Accordingly, the herbicide of the present invention can be used as a herbicide for cotton in soil treatment before the emergence of weeds or foliage treatment after the emergence of weeds.

(2) The herbicide of the present invention has the herbicidal effect against troublesome weeds such as common cocklebur and morningglory and is useful during a long period of before to after the emergence of weeds.

(3) The herbicide of the present invention is suitably decomposable in soil and gives no substantial advanse affects to the subsequent crop plants.

Now, the herbicidal activities of the herbicides of the present invention will be described with reference to Test Examples.

TEST EXAMPLE 1 (soil treatment before the emergence of weeds in upland field)

In a pot filled with soil (surface area: 600 cm$^2$), seeds of cotton (Go), barnyardgrass (Ec), Johnsongrass (So), smartweed (Po), slender amaranth (Am), lambsquarters (Ch), morningglory (Ip) and common cocklebur (Xa) were sown, tubers of purple nutsedge (Cr) were planted and covered with soil of a thickness of from 0.5 to 1 cm. One day later from the seeding, a predetermined amount of a wettable powder prepared in accordance with Formulation Example 1, was diluted with water and applied to the soil surface at a rate of 100 liters per 10 ares. The evaluation was conducted on the 20th day after the treatment. The results were evaluated in accordance with the standard as identified in Table 2 and shown by the index numbers in Tables 3 and 4.

TABLE 2

| Index No. | Herbicidal effects and Phytotoxicity |
|---|---|
| 0 | No herbicidal effect (or no phytotoxicity) |
| 1 | Herbicidal effect (or phytotoxicity): more than 0% and less than 30% |
| 2 | Herbicidal effect (or phytotoxicity): at least 30% and less than 50% |
| 3 | Herbicidal effect (or phytotoxicity): at least 50% and less than 70% |
| 4 | Herbicidal effect (or phytotoxicity): at least 70% and less than 90% |
| 5 | Herbicidal effect (or phytotoxicity): more than 90% |

TABLE 3

| Compound No. | Dose of active ingredient (gai/10a) | Phytotoxicity Go | Herbicidal effects | | | | | | | |
|---|---|---|---|---|---|---|---|---|---|---|
| | | | Ec | So | Po | Am | Ch | Ip | Xa | Cr |
| 1 | 100 | 0 | 5 | 5 | 5 | 5 | 5 | 5 | 5 | 5 |
| | 25 | 0 | 4 | 5 | 5 | 5 | 5 | 5 | 5 | 5 |
| 2 | 100 | 0 | 5 | 5 | 5 | 5 | 5 | 3 | 4 | 5 |
| | 25 | 0 | 3 | 5 | 5 | 5 | 5 | 0 | 3 | 4 |
| Comparative Compound 1 | 100 | 3 | 5 | 5 | 5 | 5 | 5 | 3 | 2 | 4 |
| | 25 | 2 | 4 | 5 | 5 | 5 | 5 | 0 | 0 | 3 |

Comparative Compound 1 will be identified below (the same applies in other Tables):

Comparative Compound 1: 2-[4,6-dimethoxypyrimidin2-yl)oxy]benzoic acid (disclosed in Japanese Unexamined Patent Publication No. 174059/1987)

TABLE 4

| Compound No. | Dose of active ingredient (gai/10a) | Phytotoxicity Go | Herbicidal effects | | | | | | | |
|---|---|---|---|---|---|---|---|---|---|---|
| | | | Ec | So | Po | Am | Ch | Ip | Xa | Cr |
| 10 | 25 | 1 | 5 | 5 | 5 | 5 | 5 | 4 | 3 | 5 |
| 11 | 100 | 1 | 5 | 5 | 5 | 5 | 5 | 4 | 4 | 5 |
| | 25 | 0 | 5 | 5 | 5 | 5 | 5 | 3 | 2 | 5 |
| 12 | 100 | 0 | 5 | 5 | 5 | 5 | 5 | 5 | 5 | 5 |
| | 25 | 0 | 5 | 5 | 5 | 5 | 5 | 5 | 4 | 5 |

TABLE 4-continued

| Compound No. | Dose of active ingredient (gai/10a) | Phytotoxicity Go | Herbicidal effects |  |  |  |  |  |  |  |
|---|---|---|---|---|---|---|---|---|---|---|
|  |  |  | Ec | So | Po | Am | Ch | Ip | Xa | Cr |
| 13 | 100 | 1 | 4 | 5 | 5 | 5 | 5 | 5 | 5 | 5 |
| 14 | 100 | 1 | 5 | 5 | 5 | 5 | 5 | 3 | 3 | 4 |
| 17 | 100 | 1 | 5 | 5 | 5 | 5 | 5 | 5 | 5 | 5 |
|  | 25 | 0 | 5 | 5 | 5 | 5 | 5 | 5 | 5 | 5 |
| 18 | 100 | 1 | 5 | 5 | 5 | 5 | 5 | 5 | 5 | 5 |
|  | 25 | 0 | 5 | 5 | 5 | 5 | 5 | 5 | 5 | 4 |
| 21 | 100 | 0 | 5 | 5 | 5 | 5 | 5 | 5 | 4 | 5 |
|  | 25 | 0 | 5 | 5 | 5 | 5 | 5 | 3 | 2 | 5 |
| 24 | 25 | 1 | 5 | 5 | 5 | 5 | 5 | 5 | 5 | 5 |
| 25 | 25 | 1 | 5 | 5 | 5 | 5 | 5 | 4 | 4 | 5 |
| 27 | 100 | 1 | 5 | 5 | 5 | 5 | 5 | 5 | 5 | 5 |
|  | 25 | 0 | 5 | 5 | 5 | 5 | 5 | 5 | 4 | 5 |
| 28 | 100 | 0 | 5 | 5 | 5 | 5 | 5 | 5 | 5 | 5 |
|  | 25 | 0 | 5 | 5 | 5 | 5 | 5 | 4 | 4 | 5 |
| Comparative Compound 1 | 100 | 3 | 5 | 5 | 5 | 5 | 5 | 2 | 2 | 4 |
|  | 25 | 3 | 4 | 4 | 5 | 5 | 5 | 0 | 0 | 2 |

TEST EXAMPLE 2 (foliage treatment after the emergence of weeds in upland field)

In a pot filled with soil (surface area: 600 cm$^2$), seeds of cotton (Go), barnyardgrass (Ec), Johnsonglass (So), smartweed (Po), slender amaranth (Am), lambsquarters(Ch), morningglory (Ip) and common cocklebur (Xa) were sown, tubers of purple nutsedge (Cr) were planted and covered with soil of a thickness of from 0.5 to 1 cm. The pot was cultured in a green house at a temperature of from 20° to 25° C. for 2 weeks, and then, a predetermined amount of a wettable powder prepared in accordance with Formulation Example 1 was diluted with water, and applied to the foliage at a rate of 100 liters per 10 ares. The evaluation was conducted on 14th day after the treatment. The results were evaluated in accordance with the standard as identified in Table 2, and shown by the index numbers in Tables 5 and 6.

TABLE 5

| Compound No. | Doses of active ingredient (gai/10a) | Phytotoxicity Go | Herbicidal effects |  |  |  |  |  |  |  |
|---|---|---|---|---|---|---|---|---|---|---|
|  |  |  | Ec | So | Po | Am | Ch | Ip | Xa | Cr |
| 1 | 100 | 1 | 5 | 5 | 5 | 5 | 5 | 5 | 5 | 5 |
|  | 25 | 0 | 4 | 5 | 5 | 5 | 5 | 5 | 5 | 5 |
| 2 | 100 | 1 | 5 | 5 | 5 | 5 | 4 | 5 | 5 | 5 |
|  | 25 | 0 | 3 | 5 | 5 | 5 | 5 | 3 | 4 | 5 |
| Comparative Compound 1 | 100 | 5 | 5 | 5 | 5 | 5 | 5 | 3 | 3 | 4 |
|  | 25 | 4 | 5 | 5 | 5 | 5 | 5 | 1 | 2 | 3 |

TABLE 6

| Compound No. | Dose of active ingredient (gai/10a) | Phytotoxicity Go | Herbicidal effects |  |  |  |  |  |  |  |
|---|---|---|---|---|---|---|---|---|---|---|
|  |  |  | Ec | So | Po | Am | Ch | Ip | Xa | Cr |
| 24 | 25 | 0 | 4 | 5 | 5 | 5 | 5 | 5 | 5 | 5 |
| 25 | 25 | 0 | 4 | 5 | 5 | 5 | 5 | 5 | 5 | 5 |
| 27 | 25 | 0 | 4 | 5 | 5 | 5 | 5 | 5 | 5 | 5 |
| 29 | 25 | 0 | 4 | 5 | 5 | 5 | 5 | 5 | 5 | 5 |
| Comparative Compound 1 | 25 | 4 | 5 | 4 | 5 | 5 | 5 | 1 | 1 | 2 |

TEST EXAMPLE 3 (foliage treatment in upland field)

In a pot filled with soil (surface area: 100 cm$^2$), seeds of barnyardgrass (Ec), crabgrass (Di), smartweed (Po), slender amaranth (Am), lambsquarters (Ch) and rice flatsedge (Ci), were sown, and covered with soil of a thickness of from 0.5 to 1 cm. The pot was cultured in a green house at a temperature of from 20° to 25° C. for 2 weeks, and then a predetermined amount of a wettable powder prepared in accordance with Formulation Example 1 was diluted with water, and applied to the foliage at a rate of 100 liters per 10 ares (dose of active ingredient: 100 g/10a). The evaluation was conducted on 14th day after the treatment with the herbicide. The results were evaluated in accordance with the standards as identified in Table 2, and shown by the index numbers in Tables 7 and 8.

TABLE 7

| Compound No. | Herbicidal effects |  |  |  |  |  |
|---|---|---|---|---|---|---|
|  | Ec | Di | Po | Am | Ch | Ci |
| 1 | 5 | 5 | 5 | 5 | 5 | 5 |
| 2 | 5 | 5 | 5 | 5 | 5 | 5 |
| Comparative Compound 1 | 5 | 5 | 4 | 5 | 5 | 5 |
| Comparative Compound 2 | 0 | 1 | 2 | 2 | 0 | 5 |
| Comparative Compound 3 | 1 | 1 | 2 | 1 | 1 | 5 |
| Comparative Compound 4 | 1 | 1 | 1 | 1 | 1 | 1 |

Comparative Compounds 2, 3 and 4 will be identified below (the same applies in other Tables):

Comparative Compound 2: ethyl-3-[(5-chloropyrimidin-2-yl)oxy]benzoate (disclosed in Japanese Unexamined Patent Publication No. 55729/1979)

Comparative Compound 3: ethyl-5[(5-chloropyrimidin-2-yl)oxy]-2-nitrobenzoate (disclosed in Japanese Unexamined Patent Publication No. 55729/1979)

Comparative Compound 4: 2-(2-tolyloxy)-4,6-dimethylpyrimidine (disclosed in Agr. and Biol. Chem. Vol. 30, No. 9, p.896)

TABLE 8

| Compound No. | Herbicidal effects | | | | | |
|---|---|---|---|---|---|---|
| | Ec | Di | Po | Am | Ch | Ci |
| 3 | 5 | 5 | 5 | 5 | 5 | 5 |
| 10 | 5 | 5 | 5 | 5 | 5 | 5 |
| 11 | 5 | 5 | 5 | 5 | 5 | 5 |
| 12 | 5 | 5 | 5 | 5 | 5 | 5 |
| 13 | 5 | 5 | 5 | 5 | 5 | 5 |
| 14 | 5 | 5 | 5 | 5 | 5 | 5 |
| 16 | 5 | 5 | 5 | 5 | 5 | 5 |
| 17 | 5 | 5 | 5 | 5 | 5 | 5 |
| 18 | 5 | 5 | 5 | 5 | 5 | 5 |
| 21 | 5 | 5 | 5 | 5 | 5 | 5 |
| 24 | 5 | 5 | 5 | 5 | 5 | 5 |
| 25 | 5 | 5 | 5 | 5 | 5 | 5 |
| 26 | 5 | 5 | 5 | 5 | 5 | 5 |
| 27 | 5 | 5 | 5 | 5 | 5 | 5 |
| 28 | 5 | 5 | 5 | 5 | 5 | 5 |
| 29 | 5 | 5 | 5 | 5 | 5 | 5 |
| 31 | 5 | 5 | 5 | 5 | 5 | 5 |
| 32 | 5 | 5 | 5 | 5 | 5 | 5 |
| Comparative Compound 2 | 0 | 1 | 2 | 1 | 1 | 5 |
| Comparative Compound 3 | 1 | 1 | 2 | 1 | 1 | 5 |
| Comparative Compound 4 | 1 | 0 | 1 | 1 | 1 | 1 |

TEST EXAMPLE 4 (soil treatment in upland field)

In a pot filled with soil (surface area: 100 cm$^2$), seeds of barnyardgrass (Ec), crabgrass (Di), smartweed (Po), slender amaranth (Am), lambsquarters (Ch) and rice flatsedge (Ci) were sown and covered with soil of a thickness of from 0.5 to 1 cm. One day later from the seeding, a predetermined amount of a wettable powder prepared in accordance with Formulation Example 1, was diluted with water and applied to the soil surface at a rate of 100 liters per 10 ares (dose of active ingredient: 100 g/10a). The evaluation was conducted on the 20th day after the treatment. The results were evaluated in accordance with the standard as identified in Table 2 and shown by the index numbers in Tables 9 and 10.

TABLE 9

| Compound No. | Herbicidal effects | | | | | |
|---|---|---|---|---|---|---|
| | Ec | Di | Po | Am | Ch | Ci |
| 1 | 5 | 5 | 5 | 5 | 5 | 5 |
| 2 | 5 | 5 | 5 | 5 | 5 | 5 |
| Comparative Compound 1 | 5 | 5 | 4 | 5 | 5 | 5 |
| Comparative Compound 2 | 0 | 0 | 0 | 0 | 0 | 5 |
| Comparative Compound 3 | 0 | 0 | 0 | 0 | 2 | 5 |
| Comparative Compound 4 | 0 | 0 | 0 | 0 | 0 | 0 |

TABLE 10

| Compound No. | Herbicidal effects | | | | | |
|---|---|---|---|---|---|---|
| | Ec | Di | Po | Am | Ch | Ci |
| 3 | 5 | 5 | 5 | 5 | 5 | 5 |
| 4 | 5 | 5 | 5 | 5 | 5 | 5 |
| 5 | 5 | 5 | 5 | 5 | 5 | 5 |
| 6 | 5 | 5 | 5 | 5 | 5 | 5 |
| 7 | 5 | 5 | 5 | 5 | 5 | 5 |
| 9 | 5 | 5 | 5 | 5 | 5 | 5 |
| 10 | 5 | 5 | 5 | 5 | 5 | 5 |
| 11 | 5 | 5 | 5 | 5 | 5 | 5 |
| 12 | 5 | 5 | 5 | 5 | 5 | 5 |
| 13 | 5 | 5 | 5 | 5 | 5 | 5 |
| 14 | 5 | 5 | 5 | 5 | 5 | 5 |
| 16 | 5 | 5 | 5 | 5 | 5 | 5 |
| 17 | 5 | 5 | 5 | 5 | 5 | 5 |
| 18 | 5 | 5 | 5 | 5 | 5 | 5 |
| 21 | 5 | 5 | 5 | 5 | 5 | 5 |
| 22 | 5 | 5 | 5 | 5 | 5 | 5 |
| 23 | 5 | 5 | 5 | 5 | 5 | 5 |
| 24 | 5 | 5 | 5 | 5 | 5 | 5 |
| 25 | 5 | 5 | 5 | 5 | 5 | 5 |
| 26 | 5 | 5 | 5 | 5 | 5 | 5 |
| 27 | 5 | 5 | 5 | 5 | 5 | 5 |
| 28 | 5 | 5 | 5 | 5 | 5 | 5 |
| 29 | 5 | 5 | 5 | 5 | 5 | 5 |
| 31 | 5 | 5 | 5 | 5 | 5 | 5 |
| Comparative Compound 2 | 0 | 0 | 0 | 0 | 0 | 5 |
| Comparative Compound 3 | 0 | 0 | 0 | 0 | 2 | 4 |
| Comparative Compound 4 | 0 | 0 | 0 | 0 | 0 | 0 |

TEST EXAMPLE 5 (test of controlling weeds in paddy field)

In a pot filled with paddy field soil, seeds of barnyardgrass (Ec), flatsedge (Cd), monochoria (Mo) and bulrush (Sc) were sown, and water was introduced to a depth of 3 cm. Two days later from the seeding, a predetermined amount of wettable powder prepared in accordance with Formulation Example 1, was diluted with water and dropwise applied to the water surface in a dose of 100g of the active ingredient per 10 ares. The evaluation was conducted on the 21st day after the treatment. The results were evaluated in accordance with the standard as identified in Table 2 and shown by the index numbers in Tables 11 and 12.

TABLE 11

| Compound No. | Herbicidal effects | | | |
|---|---|---|---|---|
| | Ec | Cd | Mo | Sc |
| 1 | 5 | 5 | 5 | 5 |
| 2 | 5 | 5 | 5 | 5 |

TABLE 12

| Compound No. | Herbicidal effects | | | |
|---|---|---|---|---|
| | Ec | Cd | Mo | Sc |
| 3 | 5 | 5 | 5 | 5 |
| 5 | 5 | 5 | 5 | 5 |
| 6 | 5 | 5 | 5 | 5 |
| 7 | 5 | 5 | 5 | 5 |
| 8 | 5 | 5 | 5 | 5 |
| 9 | 5 | 5 | 5 | 5 |
| 10 | 5 | 5 | 5 | 5 |
| 11 | 5 | 5 | 5 | 5 |
| 12 | 5 | 5 | 5 | 5 |
| 13 | 5 | 5 | 5 | 5 |
| 14 | 5 | 5 | 5 | 5 |
| 15 | 5 | 5 | 5 | 5 |
| 16 | 5 | 5 | 5 | 5 |
| 17 | 5 | 5 | 5 | 5 |
| 18 | 5 | 5 | 5 | 5 |

TABLE 12-continued

| Compound No. | Herbicidal effects | | | |
| --- | --- | --- | --- | --- |
| | Ec | Cd | Mo | Sc |
| 19 | 5 | 5 | 5 | 5 |
| 20 | 5 | 5 | 5 | 5 |
| 21 | 5 | 5 | 5 | 5 |
| 22 | 5 | 5 | 5 | 5 |
| 23 | 5 | 5 | 5 | 5 |
| 24 | 5 | 5 | 5 | 5 |
| 25 | 5 | 5 | 5 | 5 |
| 26 | 5 | 5 | 5 | 5 |
| 27 | 5 | 5 | 5 | 5 |
| 28 | 5 | 5 | 5 | 5 |
| 29 | 5 | 5 | 5 | 5 |
| 30 | 5 | 5 | 5 | 5 |
| 31 | 5 | 5 | 5 | 5 |
| 32 | 5 | 5 | 5 | 5 |
| 33 | 5 | 5 | 5 | 5 |
| 34 | 5 | 5 | 5 | 5 |

We claim:

1. A pyrimidien derivative having the formula:

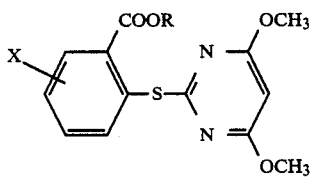

wherein X is a halogen atom, a lower alkyl group or a phenoxy group (wherein said phenoxy group may be substituted by halogen, lower alkyl or lower alkoxy), and R is a hydrogen atom, a lower alkyl group, an alkoxyalkyl group, a benzyloxyalkyl group, an alkoxycarbonyl alkyl group, a cyanoalkyl group or a

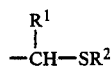

group (wherein $R^1$ is a hydrogen atom or a lower alkyl group, and $R^2$ is a lower alkyl group or a phenyl group which may be substituted by nitro), or a salt thereof.

2. The pyrimidine derivative according to claim 1, wherein X is substituted at the 6-position.

3. The pyrimidine derivative according to claim 1, wherein R is a hydrogen atom, a lower alkyl group, an alkoxyalkyl group or a benzyloxyalkyl group.

4. The pyrimidine derivative according to claim 1, which has the formula:

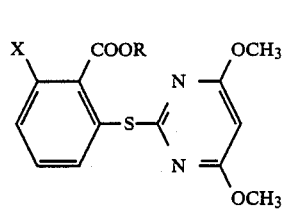

wherein R is as defined in claim 1, and X is a halogen atom or a lower alkyl group, or a salt thereof.

5. The pyrimidine derivative according to claim 4, wherein X is a halogen atom and R is a hydrogen atom, or a salt thereof.

6. The pyrimidine derivative according to claim 1, wherein the salt is an alkali metal salt, an alkaline earth metal salt, a transition metal salt or an organic ammonium salt.

7. The pyrimidine derivative according to claim 1, which has tne formula:

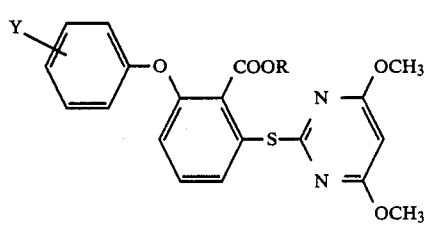

wherein R is as defined in claim 1, and Y is a hydrogen atom, a halogen atom, a lower alkyl group or a lower alkoxy group, or a salt thereof.

8. The pyrimidine derivative according to claim 1, wherein R is a hydrogen atom.

9. The pyrimidine derivative according to claim 1, which is 2-chloro-6-[(4,6-dimethoxypyrimidin-2-yl)thio]benzoic acid or its salt.

10. The pyrimidine derivative according to claim 1, wherein X is a chlorine atom, a methyl group or a fluorine atom at the 6-position.

11. A herbicidal composition comprising a herbicidally effective amount of a pyrimidine derivative of the formula I or its salt as defined in claim 1 and an agricultural adjuvant.

12. A method for killing weeds which comprises applying a herbicidally effective amount of a pyrimidine derivative of the formula I or its salt as defined in claim 1 to a locus to be protected.

* * * * *

UNITED STATES PATENT AND TRADEMARK OFFICE
CERTIFICATE OF CORRECTION

PATENT NO. :     4,923,501

DATED      :     MAY 8, 1990

INVENTOR(S) :    YOSHIHIRO SAITO ET AL.

It is certified that error appears in the above-identified patent and that said Letters Patent is hereby corrected as shown below:

On the title page:

In the inventors, delete "Kajiwaca" and insert --Kajiwara--.

Signed and Sealed this

Tenth Day of September, 1991

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,923,501
DATED     : May 8, 1990
INVENTOR(S) : Yoshihiro Saito, et. al.

It is certified that error appears in the above-indentified patent and that said Letters Patent is hereby corrected as shown below:

Column 3, line 66, Compound No. 26, "246-14 250" should read--246-250--.

Signed and Sealed this

Twenty-eighth Day of June, 1994

Attest:

BRUCE LEHMAN

*Attesting Officer*    *Commissioner of Patents and Trademarks*